United States Patent [19]

Dyckman et al.

[11] Patent Number: 5,457,244

[45] Date of Patent: Oct. 10, 1995

[54] PHENOL TAR WASTE REDUCTION PROCESS

[75] Inventors: Arkadys S. Dyckman, St. Petersburg, Russian Federation; John Fulmer, Mt. Vernon; William D. Kight, Poseyville, both of, Ind.; Andrey Zinenkov, St. Petersburg, Russian Federation; Vadim P. Boyarsky, St. Petersburg, Russian Federation; Boris I. Gorovits, St. Petersburg, Russian Federation; Leontii M. Krasnov, Novokuibishevsk, Russian Federation; Alexander S. Malinovski, Novokuibishevsk, Russian Federation; Yury I. Petrov, Novokuibishevsk, Russian Federation; Anatoly D. Sorokin, Novokuibishevsk, Russian Federation; Sergey N. Chernukhin, Novokuibishevsk, Russian Federation

[73] Assignee: General Electric Company, Pittsfield, Mass.

[21] Appl. No.: 330,149

[22] Filed: Oct. 4, 1994

[51] Int. Cl.[6] .................................................. C07C 37/68
[52] U.S. Cl. ........................ 568/754; 568/749; 568/798
[58] Field of Search ..................................... 568/754, 798, 568/749, 750, 748

[56] References Cited

U.S. PATENT DOCUMENTS

| | | | |
|---|---|---|---|
| 4,016,213 | 4/1977 | Yeh et al. | 568/754 |
| 4,173,587 | 11/1979 | Wu et al. | 568/754 |
| 4,207,264 | 6/1980 | Anderson et al. | 568/385 |
| 4,310,712 | 1/1982 | Langley | 568/798 |
| 4,351,967 | 9/1982 | Nishimura et al. | 568/754 |
| 4,358,618 | 11/1982 | Sifniades et al. | 568/385 |
| 4,929,786 | 5/1990 | Himmele et al. | 585/469 |
| 5,015,786 | 5/1991 | Araki et al. | 568/798 |
| 5,017,729 | 5/1991 | Fukuhara et al. | 568/798 |
| 5,144,094 | 9/1992 | Richmond et al. | 568/635 |
| 5,240,568 | 8/1993 | Chan et al. | 568/754 |
| 5,254,751 | 10/1993 | Zakoshansky | 568/798 |
| 5,304,684 | 4/1994 | Nishida et al. | 568/754 |
| 5,371,305 | 12/1994 | Hood | 568/798 |

FOREIGN PATENT DOCUMENTS

| | | | |
|---|---|---|---|
| 57080332 | 11/1980 | Japan. | |
| 1394452 | 5/1975 | United Kingdom | 568/754 |

OTHER PUBLICATIONS

"Side Reactions in the Phenol/Acetone Process. A Kinetic Study" Ind. Eng. Chem. Res. 1988, 27, 4–7— Pier Luigi Beltrame, Paolo Carniti, Aldo Gamba, Oscar Cappellazzo, Loreno Lorenzoni and Giuseppe Messina.

Primary Examiner—Werren B. Lone

[57] ABSTRACT

An improved phenol tar cracking process using a rectification column as a hydrocracker obtains an increased yield of valuable products, phenol, cumene and alpha-methylstyrene, by taking from 50 to 100% of the acetophenone in the reactor overhead with the cracked product stream.

11 Claims, No Drawings

PHENOL TAR WASTE REDUCTION PROCESS

This invention relates to the recovery of valuable products from waste tar produced as an unwanted by-product of the phenol/acetone from cumene process.

The method of making phenol by oxidation of cumene and catalytic cleavage of the resulting cumene hydroperoxide is well known and has replaced most of the phenol processes based on chlorination or sulfonation of benzene. More than five billion pounds per year of phenol capacity is now available in the world based on this technology.

A typical process consists of a cumene oxidation section, a CHP concentration operation, an acid-catalyzed cleavage reaction generally carried out in a fully back-mix reactor, a product neutralization and recovery section and a tar recovery system.

Many improvements directed to increasing the yield and purity of the useful products from the tar recovery step have been disclosed in the patent literature. Also, many disclosed methods describe the use of heterogeneous catalysts for replacing sulfuric acid or other mineral acids as catalysts to facilitate tar cracking which are now less desirable because of environmental regulations. These improvements have increased the recovery of phenol, cumene and alpha-methylstyrene (AMS) from the waste products causing the remaining waste tar to be decreased in volume but substantially altered in its composition.

In particular, U.S. Pat. No. 3,850,996, incorporated herein by reference, teaches the cracking of phenol tars produced over 20 years ago, in a column-type reactor with the feedstream entering the middle of the reactor and product being taken off the top. In this patent, the tar composition has a high level of para-cumyl phenol (PCP) and phenol and a relatively low level of heavy, residue. The tar composition is given in the patent as follows:

TABLE 1

|  | Feed | % |
| --- | --- | --- |
| Phenol | 630 | 15.4 |
| Acetophenone (AP) | 380 | 9.3 |
| Dimethylbenzyl Alcohol (DMBA) | 370 | 9.1 |
| PCP | 1670 | 40.9 |
| Residue | 1030 | 25.3 |
| TOTAL | 4080 | 100 |

In the twenty (20) years since the issue of this patent the many other process improvements have substantially altered the typical phenol tar composition so that phenol tar today contains a greater level of heavy residue and a reduced level of low boilers in plants employing these improvements. Also with today's advanced analytical technology the composition of tar streams from today's phenol plants can be determined in greater detail. A typical tar stream from a current phenol plant has the following composition

TABLE 2

| Light ends | <0.01% |
| --- | --- |
| Cumene | 0.02% |
| Alpha-methylstyrene (AMS) | 0.1% |
| Phenol | 16.7% |
| AP | 15.6% |
| DMBA | 5.5% |
| Alpha-methylstyrene dimers | 5.8% |
| PCP | 15.4% |
| Residue | 40.9% |

There is presently a need to obtain a greater amount of valuable products from the phenol and to reduce further the quantity of waste requiring environmentally safe disposal.

The present process meets this need by recovering a higher proportion of the valuable products, i.e., cumene, phenol and AMS, from the phenol plant tar stream. This higher recovery results from the discovery that by taking from about 50% by weight to about 100% by weight of AP overhead in the product stream the yield of valuable products is increased by about 100 kilograms per ton of phenol tar fed to the process. It is preferred to take overhead from about 70% by weight to about 100% by weight, more preferably about 90% to about 100% and most preferably about 100% of the AP. In a preferred embodiment, the reflux ratio is held in the range of from about 0 to about 2, more preferred from about 0 to about 0.5 and most preferred from about 0 to about 0.2.

In another preferred embodiment, the process is conducted at about 1 to 5 atmospheres pressure more preferably from about 1 to 3 atmospheres pressure and most preferably at about 2 atmospheres pressure. The range of temperature for operating the column-type reactor is about 275°–420° C. At temperatures below 275° C. pyrolysis is too slow to be practical, while at temperatures above 420° C. pyrolysis becomes extreme, resulting in the formation of substantial quantities of coke, which is to be avoided. However, such lower and higher temperatures as are operable are within the broader concepts of this invention. Optimum results are obtained in the range of temperatures of about 315°–325° C. No catalysts of any kind are required for the successful operation of the present thermocracking process. However, even though not necessary, the use of catalysts to promote thermocracking is not excluded from the practice of the present process.

The reactor is of conventional column-type design and may contain either sieve trays or trays with bubble caps and downcomers.

A key to the commercial practice of the present process is the low reflux ratio which rapidly removes preferably most of the AP, more preferably substantially all and, most preferably, all of the AP from the column type reactor. This is accomplished by reducing the reflux ratio below about 2. The reflux ratio is the ratio of the volume of the overhead not returned to the reactor divided by the volume of the overhead returned to the reactor. The use of low reflux ratio in the present process is directly contrary to the teachings of the prior art which employ high reflux ratios, i.e., 8 or greater.

The stream not returned to the reactor comprises AP, cumene, phenol and AMS. The AP is separated from the cumene, phenol and AMS by conventional means in a subsequent process step, typically by distillation. The cumene, phenol and AMS can then be co-mingled with other phenol process steams for further processing or can be separated from each other by conventional means and put into appropriate uses. The AP, when separated from the cumene, phenol and AMS, is of sufficient purity for commercial use or, absent commercial need for the AP, can be easily disposed of in an environmentally sound manner, usually incineration.

The following examples are provided to further illustrate the process and are not intended to be limitative thereof.

Comparative Example 1

This example is based on the teachings of U.S. Pat. No. 3,850,996. The values in Table 1 are the values found in the table of Columns 5 and 6 in the column headed "Phenol-hydrocarbons product (Conduit 58) divided by 4,080, the total of the "Feed (conduit 31)" and multiplied by 1000 to make a direct comparison with the examples of the present invention. The feed tar composition is presented in Table 1. In the Table "YVP" means yield of valuable products, i.e., cumene, phenol and AMS.

Comparative Example 2

This example is intended to illustrate the process described in U.S. Pat. No. 3,850,996 employed on the tar composition described above in Table 2.

The phenol tar composition as set forth in Table 1 above was processed in a continuous operating unit consisting of a rectification column, equipped with a total reflux head and a pot of 800 ml volume with an external reboiler, thermo-insulation coating, level sensor, and thermocouples to control the temperature in the pot and in the reboiler. On the bottom of the pot there is a valve to take off the bottom liquid. The column is a stainless steel tube filled with stainless steel spirals. It is equipped with a thermo-insulation coating and feed inlet midway between the top and bottom. The feed is directed into the rectification column acting as a thermocracker by a pump from a measured vessel. The feed rate is adjusted to provide a bottom liquid residence time in the pot of 50 hours. The pot temperature is 315°–325° C. Pressure is 2.0 atmospheres gauge. The feed tar composition is presented in Table 2. Part of the condensed overhead stream is used as a reflux and sent to the top of column. Reflux ratio is 8. The bottom liquid residence time is 50 hours. The time to reach steady state is 150 hours prior to conducting the experiment. The experiment time is 10 hours. Distillate and bottom liquid are collected continuously.

Comparative Example 3

Phenol tar processing was carried out the same as in Comparative Example 2, but using a bottom liquid residence time reduced from 50 hours to 20 hours, and the time to reach steady state was reduced from 150 to 60 hours. The feed tar composition is presented in Table 2. Experimental results are presented in Table 3.

TABLE 3

Phenol tar decomposition

Amount in distillate per 1000 kg of tar

| Components | Comparative | | | Invention | | |
|---|---|---|---|---|---|---|
| Example | 1 | 2 | 3 | 1 | 2 | 3 |
| Lights ends | | 31 | 27 | 30 | 32 | 30 |
| Cumene | 170.3 | 71 | 68 | 110 | 115 | 103 |
| AMS | 72.5 | 99 | 97 | 132 | 137 | 140 |
| Phenol | 298.5 | 105 | 97 | 154 | 165 | 168 |
| AP | 1.2 | 0.5 | 0.5 | 79 | 152 | 85 |
| DMBA | — | <0.1 | <0.1 | — | 4 | 8 |
| YVP | 541. | 275 | 262 | 396 | 417 | 411 |
| Acetophenone split, % | 1. | 0.3 | 0.3 | 50.6 | 97. | 54.5 |

Invention Example 1

Phenol tar processing was carried out the same as in Comparative Example 3, but taking off about 50% of input AP with the distillate. The feed tar composition is presented in Table 2. Experimental results are presented in Table 3.

Invention Example 2

Phenol tar processing was carried out the same as in Comparative Example 3, but taking off about 100% of input AP with the distillate. The feed tar composition is presented in Table 2. Experimental results presented in Table 3.

Invention Example 3

Phenol tar processing was carried out the same as in Invention Example 1, but at ambient atmospheric pressure. The feed tar composition is presented in Table 2. Experimental results are presented in Table 3.

In the above Invention Examples, it is shown that taking from 50 to 100% of the AP overhead increases the yield of valuable products by over 50% as compared to the use of the closest prior art procedure conducted on the same phenol tar. Although the teaching of U.S. Pat. No. 3,850,996 yields a very high level of valuable products from a phenol tar composition from a phenol plant as it operated over 20 years ago, when this same process is used on a tar stream from a modern phenol plant from which valuable products have already been recovered by other techniques, it is nowhere near as effective as the process of the present invention.

We claim:

1. An improved phenol tar recovery process comprising heating a tar stream from a phenol process based on the oxidation of cumene containing acetophenone to a temperature of from about 275° to about 420° C. in a reactor, cracking the tar and taking cracked product out of the reactor as an overhead stream, wherein the improvement comprises taking from about 50% by weight to 100% by weight of the acetophenone from the reactor as a component of the overhead stream, whereby the yield of valuable products in the overhead stream is substantially increased.

2. The process of claim 1 wherein the cracked product is refluxed and the reflux ratio is less than about 2.

3. The process of claim 1 wherein the valuable products comprise phenol, cumene and alpha-methylstyrene.

4. The process of claim 1 wherein the reactor is operated at a pressure of from about 1 to about 5 atmospheres.

5. The process of claim 1 wherein substantially all of the acetophenone is taken from the reactor in the overhead stream of cracked product.

6. The process of claim 1 wherein there is substantially no reflux.

7. The process of claim 1 wherein the tar stream is heated to a temperature of from about 315° C. to about 325° C.

8. The process of claim 1 wherein the reactor is operated at a pressure of from about 1 to about 3 atmospheres.

9. The process of claim 1 wherein the reactor is operated at a pressure of abut 2 atmospheres.

10. The process of claim 1 wherein the residence time of liquid at the bottom of the reactor is from about 20 to about 50 hours.

11. The process of claim 1 is wherein the reactor is operated at ambient atmospheric pressure.

* * * * *